(12) United States Patent
Reiley et al.

(10) Patent No.: US 6,423,083 B2
(45) Date of Patent: *Jul. 23, 2002

(54) INFLATABLE DEVICE FOR USE IN SURGICAL PROTOCOL RELATING TO FIXATION OF BONE

(75) Inventors: Mark A. Reiley, Piedmont; Arie Scholten, Fremont; Karen Talmadge, Palo Alto, all of CA (US)

(73) Assignee: Kyphon Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/059,796

(22) Filed: Apr. 13, 1998

Related U.S. Application Data

(62) Division of application No. 08/788,786, filed on Jan. 23, 1997.

(51) Int. Cl.[7] ............................................. A61B 17/56
(52) U.S. Cl. ..................... 606/192; 606/61; 604/96.01
(58) Field of Search ........................ 606/61, 191, 192; 623/17.11, 17.12, 17.15, 17.16; 604/96.01; 600/207

(56) References Cited

U.S. PATENT DOCUMENTS

| | | |
|---|---|---|
| 1,965,653 A | 7/1934 | Kennedy |
| 3,091,237 A | 5/1963 | Skinner |
| 3,112,743 A | 12/1963 | Cochran et al. |
| 3,626,949 A | 12/1971 | Shute |
| 3,648,294 A | 3/1972 | Shahrestani |

(List continued on next page.)

FOREIGN PATENT DOCUMENTS

| | | |
|---|---|---|
| DE | 3736604 | 11/1989 |
| FR | 439636 | 5/1912 |
| GB | 512456 | 9/1939 |
| NL | 9001858 | 3/1992 |
| RU | 906530 | 2/1982 |
| RU | 1148610 | 4/1985 |

OTHER PUBLICATIONS

B. Lawrence Riggs, MD et al. "Medical Progress, Involutional Osteoporosis", *The New England Journal of Medicine*, Jun. 26, 1986; pp. 1676–1686.

(List continued on next page.)

*Primary Examiner*—David Reip
(74) *Attorney, Agent, or Firm*—Ryan Kromholz & Manion, S.C.

(57) ABSTRACT

A balloon for use in compressing cancellous bone and marrow (also known as medullary bone or trabecular bone) against the inner cortex of bones whether the bones are fractured or not. The balloon comprises an inflatable, non-expandable balloon body for insertion into said bone. The body has a shape and size to compress at least a portion of the cancellous bone to form a cavity in the cancellous bone and to restore the original position of the outer cortical bone, if fractured or collapsed. The balloon is prevented from applying excessive pressure to the outer cortical bone. The wall or walls of the balloon are such that proper inflation the balloon body is achieved to provide for optimum compression of all the bone marrow. The balloon is able to be folded so that it can be inserted quickly into a bone. The balloon can be made to have a suction catheter. The main purpose of the balloon is the forming or enlarging of a cavity or passage in a bone, especially in, but not limited to, vertebral bodies.

14 Claims, 10 Drawing Sheets

U.S. PATENT DOCUMENTS

| | | |
|---|---|---|
| 3,800,788 A | 4/1974 | White |
| 3,875,595 A | 4/1975 | Froning |
| 3,889,665 A | 6/1975 | Ling et al. |
| 4,083,369 A | 4/1978 | Sinnreich |
| 4,274,163 A | 6/1981 | Malcolm et al. |
| 4,313,434 A | 2/1982 | Segal |
| 4,399,814 A | 8/1983 | Pratt, Jr. et al. |
| 4,462,394 A | 7/1984 | Jacobs |
| 4,466,435 A | 8/1984 | Murray |
| 4,467,479 A | 8/1984 | Brody |
| 4,488,549 A | 12/1984 | Lee et al. |
| 4,562,598 A | 1/1986 | Kranz |
| 4,595,006 A | 6/1986 | Burke et al. |
| 4,625,722 A | 12/1986 | Murray |
| 4,627,434 A | 12/1986 | Murray |
| 4,628,945 A | 12/1986 | Johnson, Jr. |
| 4,685,447 A | 8/1987 | Iversen et al. |
| 4,697,584 A | 10/1987 | Haynes |
| 4,706,670 A | 11/1987 | Andersen et al. |
| 4,714,478 A | 12/1987 | Fischer |
| 4,772,287 A | 9/1988 | Ray et al. |
| 4,888,022 A | 12/1989 | Huebsch |
| 4,888,024 A | 12/1989 | Powlan |
| 4,892,550 A | 1/1990 | Huebsch |
| 4,896,662 A | 1/1990 | Noble |
| 4,969,888 A | 11/1990 | Scholten et al. |
| 5,053,035 A | 10/1991 | McLaren |
| 5,071,435 A | 12/1991 | Fuchs et al. |
| 5,102,413 A | 4/1992 | Poddar |
| 5,108,404 A | 4/1992 | Scholten et al. |
| 5,147,366 A | 9/1992 | Arroyo et al. |
| 5,163,989 A | 11/1992 | Campbell et al. |
| 5,176,683 A | 1/1993 | Kimsey et al. |
| 5,176,692 A | 1/1993 | Wilk et al. |
| 5,303,718 A | 4/1994 | Krajicek |
| 5,330,429 A | 7/1994 | Noguchi et al. |
| 5,331,975 A | 7/1994 | Bonotti |
| 5,361,752 A | 11/1994 | Moll et al. |
| 5,383,932 A | 1/1995 | Wilson et al. |
| 5,423,850 A | 6/1995 | Berger |
| 5,441,538 A | 8/1995 | Bonutti |
| 5,454,365 A | 10/1995 | Bonutti |
| 5,468,245 A | 11/1995 | Vargas, III |
| 5,480,400 A | 1/1996 | Berger |
| 5,514,143 A | 5/1996 | Bonutti et al. |
| 5,514,153 A | 5/1996 | Bonutti |
| 5,522,790 A | 6/1996 | Moll et al. |
| 5,522,846 A | 6/1996 | Bonutti |
| 5,527,343 A | 6/1996 | Bonutti |
| 5,527,624 A | 6/1996 | Higgins et al. |
| 5,531,856 A | 7/1996 | Moll et al. |
| 5,540,711 A | 7/1996 | Kieturakis et al. |
| 5,545,222 A | 8/1996 | Bonutti |
| 5,549,679 A | 8/1996 | Kuslich |
| 5,562,736 A | 10/1996 | Ray et al. |
| 5,571,109 A | 11/1996 | Bertagnoli |
| 5,571,189 A | 11/1996 | Kuslich |
| 6,017,305 A * | 1/2000 | Bonutti ..................... 606/192 |
| 6,066,154 A * | 5/2000 | Reiley et al. ............... 606/192 |

OTHER PUBLICATIONS

L. Cohen, MD "Fractures of the Osteoporotic Spine", Pathologic Fractures in Betabolic Bone Disease, *The Orthopedic Clinics of N. America*, vol. 21:1, Jan. 1990, pp. 143–152.

S.L. Silverman, "The Clinical Consequences of Vertebral Compression Fracture", *Bone*, 13, S27–S31 (1992).

Melton, III, et al., "Perspective: How Many Woman Have Osteoporosis", *Journal of Bone and Mineral Research*, vol. 7, No. 9 1992, pp. 1005–1010.

K. Harrington, The Use of Methylmethacrylate as an Adjunct in the Internal Fixation of Malignant Neoplastic Fractures, *The Journal of Bone and Joint Surgery*, vol. 54A, No. 8, Dec. 1972; pp. 1665–1676.

Instructions entitled "Exeter Pressurizer System", Howmedica Inc, Orthopaedics Division, 1979; 2 pages.

* cited by examiner

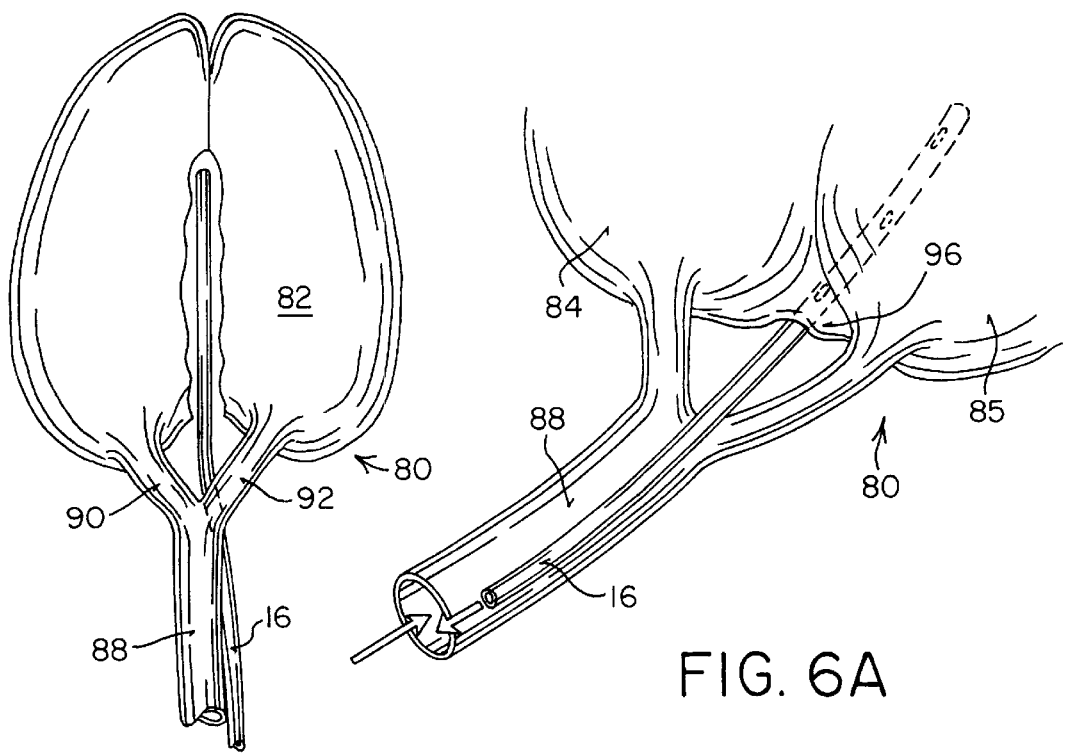
FIG. 6
FIG. 6A
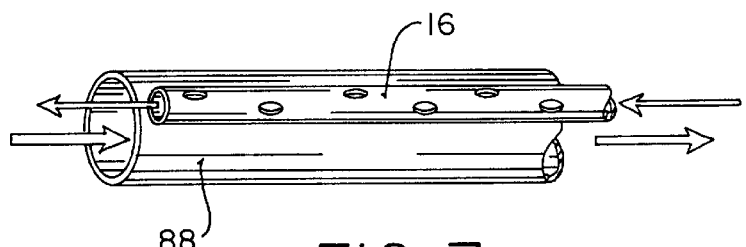
FIG. 7
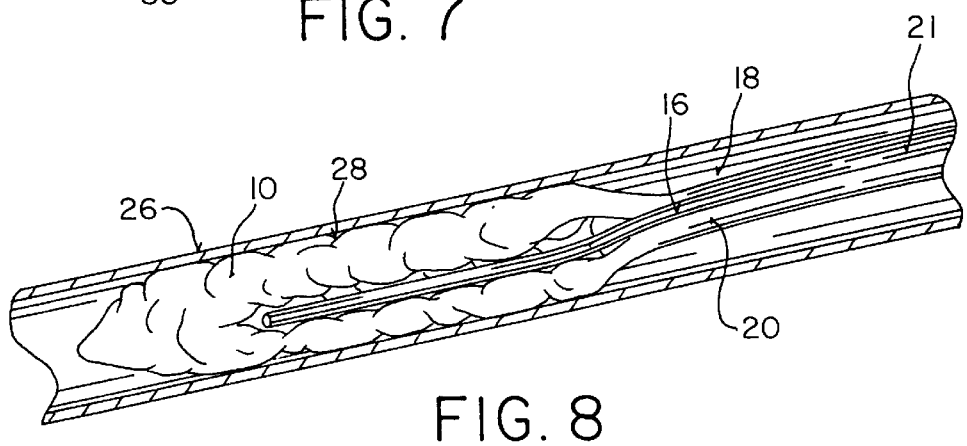
FIG. 8

INFLATABLE DEVICE FOR USE IN SURGICAL PROTOCOL RELATING TO FIXATION OF BONE

Divisional application under 37 CFR 1.60, of pending prior application Ser. No. 08/788,786 filed on Jan. 23, 1997.

This invention relates to improvements in the surgical treatment of bone conditions of the human and other animal bone systems and, more particularly, to an inflatable balloon-like device for use in treating such bone conditions. Osteoporosis, avascular necrosis and bone cancer are diseases of bone that predispose the bone to fracture or collapse. There are 2 million fractures each year in the United States, of which about 1.3 million are caused by osteoporosis. Avascular necrosis and bone cancers are more rare but can cause bone problems that are currently poorly addressed.

BACKGROUND OF THE INVENTION

In U.S. Pat. Nos. 4,969,888 and 5,108,404, an apparatus and method are disclosed for the fixation of fractures or other conditions of human and other animal bone systems, both osteoporotic and non-osteoporotic. The apparatus and method are especially suitable for use in the fixation of, but not limited to, vertebral body compression fractures, Colles fractures and fractures of the proximal humerus.

The method disclosed in these two patents includes a series of steps which a surgeon or health care provider can perform to form a cavity in pathological bone (including but not limited to osteoporotic bone, osteoporotic fractured metaphyseal and epiphyseal bone, osteoporotic vertebral bodies, fractured osteoporotic vertebral bodies, fractures of vertebral bodies due to tumors especially round cell tumors, avascular necrosis of the epiphyses of long bones, especially avascular necrosis of the proximal femur, distal femur and proximal humerus and defects arising from endocrine conditions).

The method further includes an incision in the skin (usually one incision, but a second small incision may also be required if a suction egress is used) followed by the placement of a guide pin which is passed through the soft tissue down to and into the bone.

The method further includes drilling the bone to be treated to form a cavity or passage in the bone, following which an inflatable balloon-like device is inserted into the cavity or passage and inflated. The inflation of the inflatable device causes a compacting of the cancellous bone and bone marrow against the inner surface of the cortical wall of the bone to further enlarge the cavity or passage. The inflatable device is then deflated and then is completely removed from the bone. A smaller inflatable device (a starter balloon) can be used initially, if needed, to initiate the compacting of the bone marrow and to commence the formation of the cavity or passage in the cancellous bone and marrow. After this has occurred, a larger, inflatable device is inserted into the cavity or passage to further compact the bone marrow in all directions.

A flowable biocompatible filling material, such as methylmethacrylate cement or a synthetic bone substitute, is then directed into the cavity or passage and allowed to set to a hardened condition to provide structural support for the bone. Following this latter step, the insertion instruments are removed from the body and the incision in the skin is covered with a bandage.

While the apparatus and method of the above patents provide an adequate protocol for the fixation of bone, it has been found that the compacting of the bone marrow and/or the trabecular bone and/or cancellous bone against the inner surface of the cortical wall of the bone to be treated can be significantly improved with the use of inflatable devices that incorporate additional engineering features not heretofore described and not properly controlled with prior inflatable devices in such patents. A need has therefore arisen for improvements in the shape, construction and size of inflatable devices for use with the foregoing apparatus and method, and the present invention satisfies such need.

Prior Techniques for the Manufacture of Balloons for In-Patient Use

A review of the prior art relating to the manufacture of balloons shows that a fair amount of background information has been amassed in the formation of guiding catheters which are introduced into cardiovascular systems of patients through the brachial or femoral arteries. However, there is a scarcity of disclosures relating to inflatable devices used in bone, and none for compacting bone marrow in vertebral bodies and long bones.

In a dilatation catheter, the catheter is advanced into a patient until a balloon is properly positioned across a lesion to be treated. The balloon is inflated with a radiopaque liquid at pressures above four atmospheres to compress the plaque of the lesion to thereby dilate the lumen of the artery. The balloon can then be deflated, then removed from the artery so that the blood flow can be restored through the dilated artery.

A discussion of such catheter usage technique is found and clearly disclosed in U.S. Pat. No. 5,163,989. Other details of angioplasty catheter procedures, and details of balloons used in such procedures can be found in U.S. Pat. Nos. 4,323,071, 4,332,254, 4,439,185, 4,168,224, 4,516,672, 4,538,622, 4,554,929, and 4,616,652.

Extrusions have also been made to form prism shaped balloons using molds which require very accurate machining of the interior surface thereof to form acceptable balloons for angioplastic catheters. However, this technique of extrusion forms parting lines in the balloon product which parting lines are limiting in the sense of providing a weak wall for the balloon itself.

U.S. Pat. No. 5,163,989 discloses a mold and technique for molding dilatation catheters in which the balloon of the catheter is free of parting lines. The technique involves inflating a plastic member of tubular shape so as to press it against the inner molding surface which is heated. Inflatable devices are molded into the desired size and shape, then cooled and deflated to remove it from the mold. The patent states that, while the balloon of the present invention is especially suitable for forming prism-like balloons, it can also be used for forming balloons of a wide variety of sizes and shapes.

A particular improvement in the catheter art with respect to this patent, namely U.S. Pat. No. 4,706,670, is the use of a coaxial catheter with inner and outer tubing formed and reinforced by continuous helical filaments. Such filaments cross each other causing the shaft of the balloon to become shorter in length while the moving portion of the shank becomes longer in length. By suitably balancing the lengths and the angle of the weave of the balloon and moving portions of the filaments, changes in length can be made to offset each other. Thus, the position of the inner and outer tubing can be adjusted as needed to keep the balloon in a desired position in the blood vessel.

Other disclosures relating to the insertion of inflatable devices for treating the skeleton of patients include the following;

U.S. Pat. No. 4,313,434 relates to the fixation of a long bone by inserting a deflated flexible bladder into a medullary cavity, inflating the balloon bladder, sealing the interior of the long bone until healing has occurred, then removing the bladder and filling the opening through which the bladder emerges from the long bone.

U.S. Pat. No. 5,102,413 discloses the way in which an inflatable bladder is used to anchor a metal rod for the fixation of a fractured long bone.

Other references which disclose the use of balloons and cement for anchoring of a prosthesis include U.S. Pat. Nos. 5,147,366, 4,892,550, 4,697,584, 4,562,598, and 4,399,814.

A Dutch patent, NL 901858, discloses a means for fracture repair with a cement-impregnated bag which is inflated into a preformed cavity and allowed to harden.

It can be concluded from the foregoing review of the prior art that there is little or no substantive information on inflatable devices used to create cavities in bone. It does not teach the shape of the balloon which creates a cavity that best supports the bone when appropriately filled. It does not teach how to prevent balloons from being spherical when inflated, when this is desired. Current medical balloons can compress bone but are too small and generally have the wrong configuration and are generally not strong enough to accomplish adequate cavity formation in either the vertebral bodies or long bones of the body.

U.S. Pat. Nos. 4,969,888 and 5,108,404 disclose a checker-shaped balloon for compressing cancellous bone, but does not provide information on how this balloon remains in its shape when inflated.

Thus, the need continues for an improved inflatable device for use with pathological bones and the treatment thereof.

SUMMARY OF THE INVENTION

The present invention is directed to a balloon-like inflatable device or balloon for use in carrying out the apparatus and method of the above-mentioned patents U.S. Pat. Nos. 4,969,888 and 5,108,404. Such inflatable devices, hereinafter sometimes referred to as balloons, have shapes for compressing cancellous bone and marrow (also known as medullary bone or trabecular bone) against the inner cortex of bones whether the bones are fractured or not.

In particular, the present invention is directed to a balloon for use in treating a bone predisposed to fracture or to collapse. The balloon comprises an inflatable, non-expandable balloon body for insertion into said bone. The body has a predetermined shape and size when substantially inflated sufficient to compress at least a portion of the inner cancellous bone to create a cavity in the cancellous bone and to restore the original position of the outer cortical bone, if fractured or collapsed. The balloon body is restrained to create said predetermined shape and size so that the fully inflated balloon body is prevented from applying substantial pressure to the inner surface of the outer cortical bone if said bone is unfractured or uncollapsed.

In addition to the shape of the inflatable device itself, another aspect of importance is the construction of the wall or walls of the balloon such that proper inflation the balloon body is achieved to provide for optimum compression of all the bone marrow. The material of the balloon is also desirably chosen so as to be able to fold the balloon so that it can be inserted quickly and easily into a bone using a guide pin and a cannula, yet can also withstand high pressures when inflated. The balloon can also include optional ridges or indentations which are left in the cavity after the balloon has been removed, to enhance the stability of the filler. Also, the inflatable device can be made to have an optional, built-in suction catheter. This is used to remove any fat or fluid extruded from the bone during balloon inflation in the bone. Also, the balloon body can be protected from puncture by the cortical bone or canula by being covered while inside the canula with an optional protective sleeve of suitable material, such as Kevlar or PET or other polymer or substance that can protect the balloon. The main purpose of the inflatable device, therefore, is the forming or enlarging of a cavity or passage in a bone, especially in, but not limited to, vertebral bodies.

The primary object of the present invention is to provide an improved balloon-like inflatable device for use in carrying out a surgical protocol of cavity formation in bones to enhance the efficiency of the protocol, to minimize the time prior to performing the surgery for which the protocol is designed and to improve the clinical outcome. These balloons approximate the inner shape of the bone they are inside of in order to maximally compress cancellous bone. They have additional design elements to achieve specific clinical goals. Preferably, they are made of inelastic material and kept in their defined configurations when inflated, by various restraints, including (but not limited to) use of inelastic materials in the balloon body, seams in the balloon body created by bonding or fusing separate pieces of material together, or by fusing or bonding together opposing sides of the balloon body, woven material bonded inside or outside the balloon body, strings or bands placed at selected points in the balloon body, and stacking balloons of similar or different sizes or shapes on top of each other by gluing or by heat fusing them together. Optional ridges or indentations created by the foregoing structures, or added on by bonding additional material, increases stability of the filler. Optional suction devices, preferably placed so that if at least one hole is in the lowest point of the cavity being formed, will allow the cavity to be cleaned before filling.

Among the various embodiments of the present invention are the following:

1. A doughnut (or torus) shaped balloon with an optional built-in suction catheter to remove fat and other products extruded during balloon expansion.

2. A balloon with a spherical outer shape surrounded by a ring-shaped balloon segment for body cavity formation.

3. A balloon which is kidney bean shaped in configuration. Such a balloon can be constructed in a single layer, or several layers stacked on top of each other.

4. A spherically shaped balloon approximating the size of the head of the femur (i.e. the proximal femoral epiphysis). Such a balloon can also be a hemisphere.

5. A balloon in the shape of a humpbacked banana or a modified pyramid shape approximating the configuration of the distal end of the radius (i.e. the distal radial epiphysis and metaphysis).

6. A balloon in the shape of a cylindrical ellipse to approximate the configuration of either the medial half or the lateral half of the proximal tibial epiphysis. Such a balloon can also be constructed to approximate the configuration of both halves of the proximal tibial epiphysis.

7. A balloon in the shape of sphere on a base to approximate the shape of the proximal humeral epiphysis and metaphysis with a plug to compress cancellous bone into the diaphysis, sealing it off.

8. A balloon device with optional suction device.

9. Protective sheaths to act as puncture guard members optionally covering each balloon inside its catheter.

The present invention, therefore, provides improved, inflatable devices for creating or enlarging a cavity or passage in a bone wherein the devices are inserted into the bone. The configuration of each device is defined by the surrounding cortical bone and adjacent internal structures, and is designed to occupy about 70–90% of the volume of the inside of the bone, although balloons that are as small as about 40% and as large as about 99% are workable for fractures. In certain cases, usually avascular necrosis, the balloon size may be as small as 10% of the cancellous bone volume of the area of bone being treated, due to the localized nature of the fracture or collapse. The fully expanded size and shape of the balloon is limited by additional material in selected portions of the balloon body whose extra thickness creates a restraint as well as by either internal or external restraints formed in the device including, but not limited to, mesh work, a winding or spooling of material laminated to portions of the balloon body, continuous or non-continuous strings across the inside held in place at specific locations by glue inside or by threading them through to the outside and seams in the balloon body created by bonding two pieces of body together or by bonding opposing sides of a body through glue or heat. Spherical portions of balloons may be restrained by using inelastic materials in the construction of the balloon body, or may be additionally restrained as just described. The material of the balloon is preferably a non-elastic material, such as polyethylene tetraphthalate (PET), Kevlar or other patented medical balloon materials. It can also be made of semi-elastic materials, such as silicone or elastic material such as latex, if appropriate restraints are incorporated. The restraints can be made of a flexible, inelastic high tensile strength material including, but not limited, to those described in U.S. Pat. No. 4,706,670. The thickness of the balloon wall is typically in the range of $2/1000$ ths to $25/1000$ ths of an inch, or other thicknesses that can withstand pressures of up to 250–400 psi.

A primary goal of percutaneous vertebral body augmentation of the present invention is to provide a balloon which can create a cavity inside the vertebral body whose configuration is optimal for supporting the bone. Another important goal is to move the top of the vertebral body back into place to retain height where possible, however, both of these objectives must be achieved without fracturing the cortical wall of the vertebral body. This feature could push vertebral bone toward the spinal cord, a condition which is not to be desired.

The present invention satisfies these goals through the design of inflatable devices to be described. Inflating such a device compresses the calcium-containing soft cancellous bone into a thin shell that lines the inside of the hard cortical bone creating a large cavity.

At the same time, the biological components (red blood cells, bone progenitor cells) within the soft bone are pressed out and removed by rinsing during the procedure. The body recreates the shape of the inside of an unfractured vertebral body, but optimally stops at approximately 70 to 90% of the inner volume. The balloons of the present invention are inelastic, so maximally inflating them can only recreate the predetermined shape and size. However, conventional balloons become spherical when inflated. Spherical shapes will not allow the hardened bone cement to support the spine adequately, because they make single points of contact on each vertebral body surface (the equivalent of a circle inside a square, or a sphere inside a cylinder). The balloons of the present invention recreate the flat surfaces of the vertebral body by including restraints that keep the balloon in the desired shape. This maximizes the contacts between the vertebral body surfaces and the bone cement, which strengthens the spine. In addition, the volume of bone cement that fills these cavities creates a thick mantle of cement (4 mm or greater), which is required for appropriate compressive strength. Another useful feature, although not required, are ridges in the balloons which leave their imprint in the lining of compressed cancellous bone. The resulting bone cement "fingers" provide enhanced stability.

The balloons which optimally compress cancellous bone in vertebral bodies are the balloons listed as balloon types 1, 2 and 3 above. These balloons are configured to approximate the shape of the vertebral body. Since the balloon is chosen to occupy 70 to 90% of the inner volume, it will not exert undue pressure on the sides of the vertebral body, thus the vertebral body will not expand beyond its normal size (fractured or unfractured). However, since the balloon has the height of an unfractured vertebral body, it can move the top, which has collapsed, back to its original position.

A primary goal of percutaneous proximal humeral augmentation is to create a cavity inside the proximal humerus whose configuration is optimal for supporting the proximal humerus. Another important goal is to help realign the humeral head with the shaft of the humerus when they are separated by a fracture. Both of these goals must be achieved by exerting pressure primarily on the cancellous bone, and not the cortical bone. Undue pressure against the cortical bone could conceivably cause a worsening of a shoulder fracture by causing cortical bone fractures.

The present invention satisfies these goals through the design of the inflatable devices to be described. Inflating such a device compresses the cancellous bone against the cortical walls of the epiphysis and metaphysis of the proximal humerus thereby creating a cavity. In some cases, depending on the fracture location, the balloon or inflatable device may be used to extend the cavity into the proximal part of the humeral diaphysis.

Due to the design of the "sphere on a stand" balloon (described as number 7 above), the cavity made by this balloon recreates or approximates the shape of the inside cortical wall of the proximal humerus. The approximate volume of the cavity made by the "spherical on a stand balloon" is 70 to 90% that of the proximal humeral epiphysis and metaphysis, primarily, but not necessarily exclusive of, part of the diaphysis. The shape approximates the shape of the humeral head. The "base" is designed to compress the trabecular bone into a "plug" of bone in the distal metaphysis or proximal diaphysis. This plug of bone will prevent the flow of injectable material into the shaft of the humerus, improving the clinical outcome. The sphere can also be used without a base.

A primary goal of percutaneous distal radius augmentation is to create a cavity inside the distal radius whose configuration is optimal for supporting the distal radius. Another important goal is to help fine tune fracture realignment after the fracture has been partially realigned by finger traps. Both of these goals must be achieved by exerting pressure primarily on the cancellous bone and not on the cortical bone. Excessive pressure against the cortical bone could conceivably cause cortical bone fractures, thus worsening the condition.

The present invention satisfies these goals through the design of inflatable devices either already described or to be described.

The design of the "humpbacked banana", or modified pyramid design (as described as number 5 above), approximates the shape of the distal radius and therefore, the cavity made by this balloon approximates the shape of the distal radius as well. The approximate volume of the cavity to be made by this humpbacked banana shaped balloon is 70 to 90% that of the distal radial epiphysis and metaphysis primarily of, but not necessarily exclusive of, some part of the distal radial diaphysis. Inflating such a device compresses the cancellous bone against the cortical walls of the epiphysis and metaphysis of the distal radius in order to create a cavity. In some cases, depending on the fracture location, the osseous balloon or inflatable device may be used to extend the cavity into the distal part of the radial diaphysis.

A primary goal of percutaneous femoral head (or humeral head) augmentation is to create a cavity inside the femoral head (or humeral head) whose configuration is optimal for supporting the femoral head. Another important goal is to help compress avascular (or aseptic) necrotic bone or support avascular necrotic bone is the femoral head. This goal may include the realignment of avascular bone back into the position it previously occupied in the femoral head in order to improve the spherical shape of the femoral head. These goals must be achieved by exerting pressure primarily on the cancellous bone inside the femoral head.

The present invention satisfied these goals through the design of inflatable devices either already described or to be described.

The design of the spherical osseous balloon (described as balloon type 4 above) approximates the shape of the femoral head and therefore creates a cavity which approximates the shape of the femoral head as well. (It should be noted that the spherical shape of this inflatable device also approximates the shape of the humeral head and would, in fact, be appropriate for cavity formation in this osseous location as well.) Inflating such a device compresses the cancellous bone of the femoral head against its inner cortical walls in order to create a cavity. In some cases, depending upon the extent of the avascular necrosis, a smaller or larger cavity inside the femoral head will be formed. In some cases, if the area of avascular necrosis is small, a small balloon will be utilized which might create a cavity only 10 to 15% of the total volume of the femoral head. If larger areas of the femoral head are involved with the avascular necrosis, then a larger balloon would be utilized which might create a much larger cavity, approaching 80 to 90% of the volume of the femoral head.

The hemispherical balloon approximates the shape of the top half of the femoral (and humeral) head, and provides a means for compacting cancellous bone in an area of avascular necrosis or small fracture without disturbing the rest of the head. This makes it easier to do a future total joint replacement if required.

A primary goal of percutaneous proximal tibial augmentation is to create a cavity inside the proximal tibia whose configuration is optimal for supporting either the medial or lateral tibial plateaus. Another important goal is to help realign the fracture fragments of tibial plateau fractures, particularly those features with fragments depressed below (or inferior to) their usual location. Both of these objectives must be achieved by exerting pressure on primarily the cancellous bone and not the cortical bone. Pressure on the cortical bone could conceivably cause worsening of the tibial plateau fracture.

The present invention satisfies these goals through the design of the inflatable devices to be described. Inflating such a device compresses the cancellous bone against the cortical walls of the medial or lateral tibial plateau in order to create a cavity.

Due to the design of the "elliptical cylinder" balloon (described as balloon type 6 above) the cavity made by this balloon recreates or approximates the shape of the cortical walls of either the medial or lateral tibial plateaus. The approximate volume of the cavity to be made by the appropriate elliptical cylindrical balloon is 50 to 90% of the proximal epiphyseal bone of either the medial half or the lateral half of the tibial.

Other objects of the present invention will become apparent as the following specification progresses reference being had to the accompanying drawings for an illustration of the invention.

BRIEF DESCRIPTION OF THE DRAWINGS

FIG. 6 shows an oblong-shaped balloon with a catheter extending into the central portion of the balloon;

FIG. 6A is a perspective view of the way in which a catheter is arranged relative to the inner tubes for inflating the balloon of FIG. 6;

FIG. 7 is a suction tube and a contrast injection tube for carrying out the inflation of the balloon and removal of debris caused by expansion from the balloon itself;

FIG. 8 is a vertical section through a balloon after it has been deflated and as it is being inserted into the vertebral body of a human;

DETAILED DESCRIPTION OF THE PREFERRED EMBODIMENT

Balloons for Vertebral Bodies

A first embodiment of the balloon (FIG. 1) of the present invention is broadly denoted by the numeral 10 and includes a balloon body 11 having a pair of hollow, inflatable, non-expandable parts 12 and 14 of flexible material, such as PET or Kevlar. Parts 12 and 14 have a suction tube 16 therebetween for drawing fats and other debris by suction into tube 16 for transfer to a remote disposal location. Catheter 16 has one or more suction holes so that suction may be applied to the open end of tube 16 from a suction source (not shown).

Figure 1:
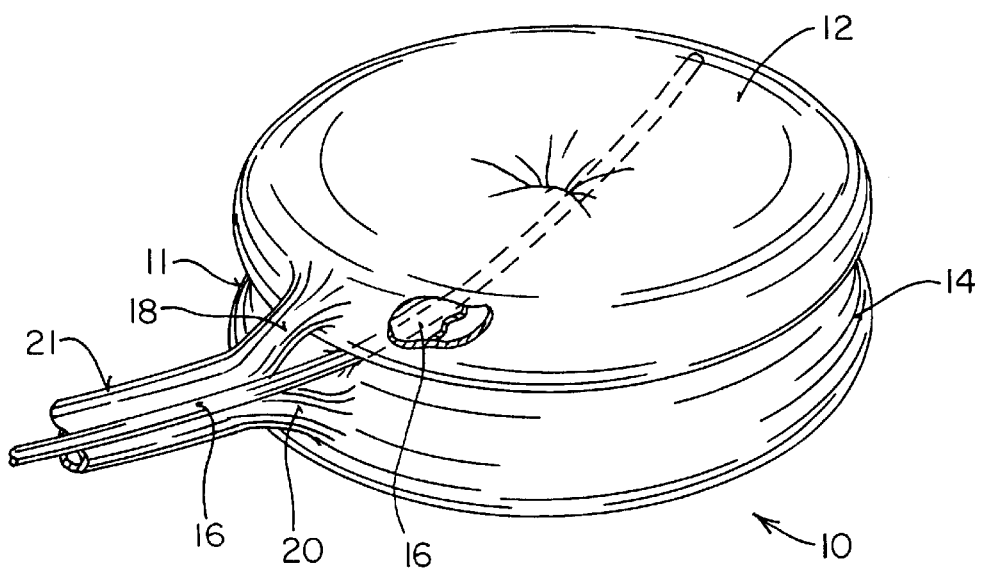
FIG. 1 is a perspective view of a first embodiment of the balloon of the present invention, the embodiment being in the shape of a stacked doughnut assembly.

The parts 12 and 14 are connected together by an adhesive which can be of any suitable type. Parts 12 and 14 are doughnut-shaped as shown in FIG. 1 and have tubes 18 and 20 which communicate with and extend away from the parts 12 and 14, respectively, to a source of inflating liquid under pressure (not shown). The liquid can be any sterile biocompatible solution. The liquid inflates the balloon 10, particularly parts 12 and 14 thereof after the balloon has been inserted in a collapsed condition (FIG. 8) into a bone to be treated, such as a vertebral bone 22 in FIG. 2. The above-mentioned U.S. Pat. Nos. 4,969,888 and 5,108,404 disclose the use of a guide pin and cannula for inserting the balloon into bone to be treated when the balloon is deflated and has been inserted into a tube and driven by the catheter into the cortical bone where the balloon is inflated.

FIG. 8 shows a deflated balloon 10 being inserted through a cannula 26 into bone. The balloon in cannula 26 is deflated and is forced through the cannula by exerting manual force on the catheter 21 which extends into a passage 28 extending into the interior of the bone. The catheter is slightly flexible but is sufficiently rigid to allow the balloon to be forced into the interior of the bone where the balloon is then inflated by directing fluid into tube 88 whose outlet ends are coupled to respective parts 12 and 14.

Figure 2:
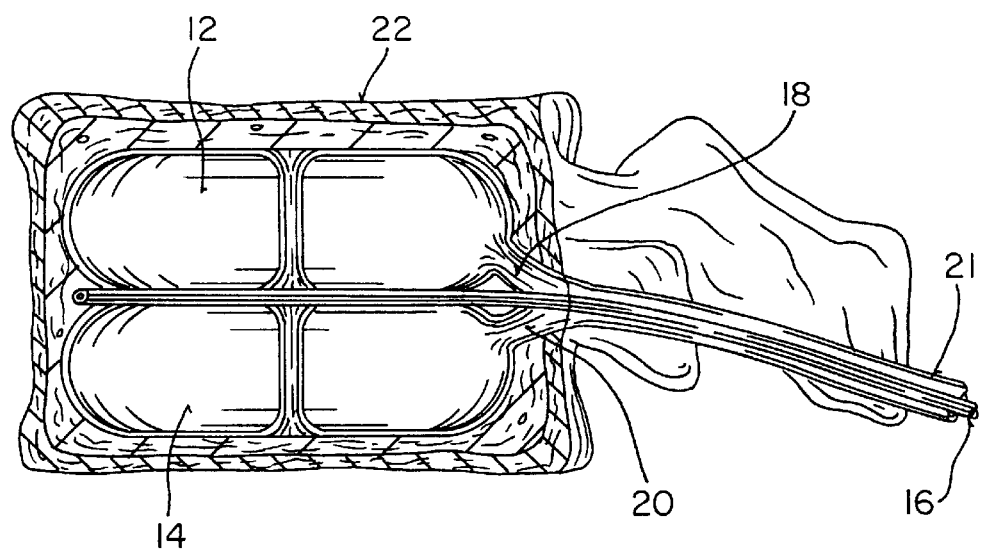
FIG. 2 is a vertical section through the balloon of FIG. 1 showing the way in which the doughnut portions of the balloon of FIG. 1, fit into a cavity of a vertebral body.

In use, balloon 10 is initially deflated and, after the bone to be filled with the balloon has been prepared to receive the balloon with drilling, the deflated balloon is forced into the bone in a collapsed condition through cannula 26. The bone is shown in FIG. 2. The balloon is oriented preferably in the bone such that it allows minimum pressure to be exerted on the bone marrow and/or cancellous bone if there is no fracture or collapse of the bone. Such pressure will compress the bone marrow and/or cancellous bone against the inner wall of the cortical bone, thereby compacting the bone marrow of the bone to be treated and to further enlarge the cavity in which the bone marrow is to be replaced by a biocompatible, flowable bone material.

The balloon is then inflated to compact the bone marrow and/or cancellous bone in the cavity and, after compaction of the bone marrow and/or cancellous bone, the balloon is deflated and removed from the cavity. While inflation of the balloon and compaction occurs, fats and other debris are sucked out of the space between and around parts 12 and 14 by applying a suction force to catheter tube 16. Following this, and following the compaction of the bone marrow, the balloon is deflated and pulled out of the cavity by applying a manual pulling force to the catheter tube 21.

Figure 4:
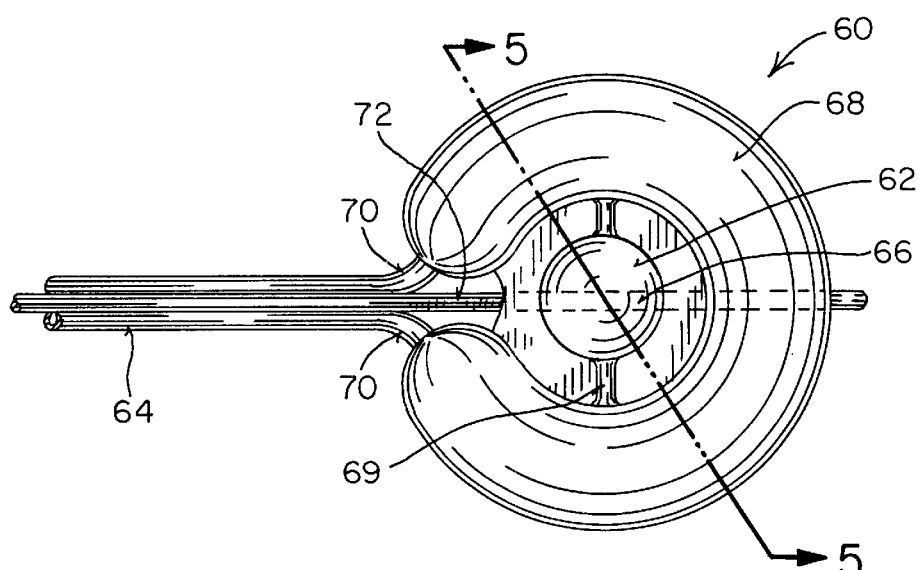
FIG. 4 is a top plan view of a spherical balloon having a cylindrical ring surrounding the balloon.
Figure 5:
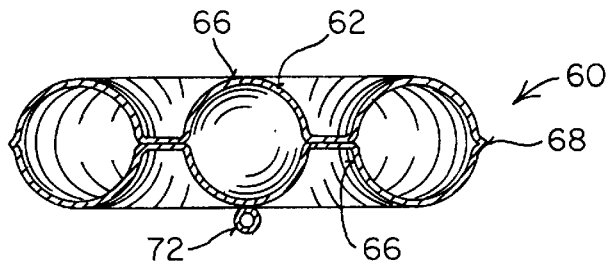
FIG. 5 is a vertical section through the spherical balloon and ring of FIG. 4.

The second embodiment of the inflatable device of the present invention is broadly denoted by the numeral 60 and is shown in FIGS. 4 and 5. Balloon 60 includes a central spherical part 62 which is hollow and which receives an inflating liquid under pressure through a tube 64. The spherical part is provided with a spherical outer surface 66 and has an outer periphery which is surrounded substantially by a ring shaped part 68 having tube segments 70 for inflation of part 68. A pair of passages 69 interconnect parts 62 and 68. A suction tube segment 72 draws liquid and debris from the bone cavity being formed by the balloon 60.

Figure 9:
FIGS. 9 and 9A are side elevational views of a cannula showing how the protective sleeve or guard member expands when leaving the cannula.
Figure 9B:
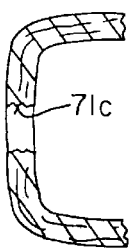
FIG. 9B is a vertical section through a vertebral bone into which an access hole has been drilled.
Figure 9A:
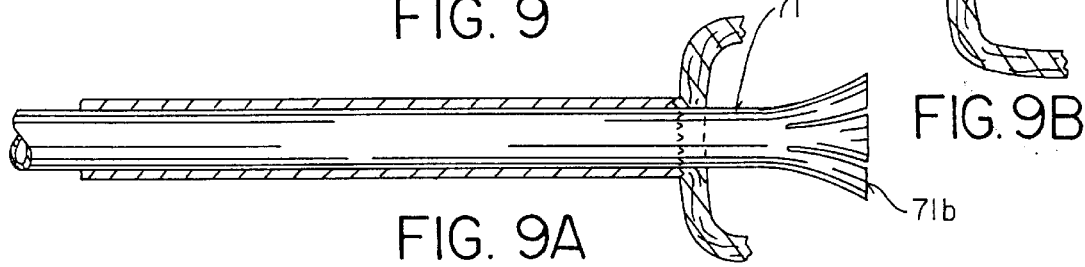

Provision can be made for a balloon sleeve 71 for balloon 60 and for all balloons disclosed herein. A balloon sleeve 71 (FIG. 9) is shiftably mounted in an outer tube 71a and can be used to insert the balloon 60 when deflated into a cortical bone. The sleeve 71 has resilient fingers 71b which bear against the interior of the entrance opening 71c of the vertebral bone 22 (FIG. 9A) to prevent tearing of the balloon. Upon removal of the balloon sleeve, liquid under pressure will be directed into tube 64 which will inflate parts 62 and 68 so as to compact the bone marrow within the cortical bone. Following this, balloon 60 is deflated and removed from the bone cavity.

FIGS. 6 and 6A show several views of a modified doughnut shape balloon 80 of the type shown in FIGS. 1 and 2, except the doughnut shapes of balloon 80 are not stitched onto one another. In FIG. 6, balloon 80 has a pear-shaped outer convex surface 82 which is made up of a first hollow part 84 and a second hollow part 85. A tube 88 is provided for directing liquid into the two parts along branches 90 and 92 to inflate the parts after the parts have been inserted into the medullary cavity of a bone. A catheter tube 16 is inserted into the space 96 between two parts of the balloon 80. An adhesive bonds the two parts 84 and 85 together at the interface thereof.

FIG. 6A shows the way in which the catheter tube 16 is inserted into the space or opening 96 between the two parts of the balloon 80.

FIG. 7 shows tube 88 of which, after directing inflating liquid into the balloon 80, can inject contrast material into the balloon 80 so that x-rays can be taken of the balloon with the inflating material therewithin to determine the proper placement of the balloon. Tube 16 is also shown in FIG. 6, it being attached in some suitable manner to the outer side wall surface of tube 88.

Figure 3:
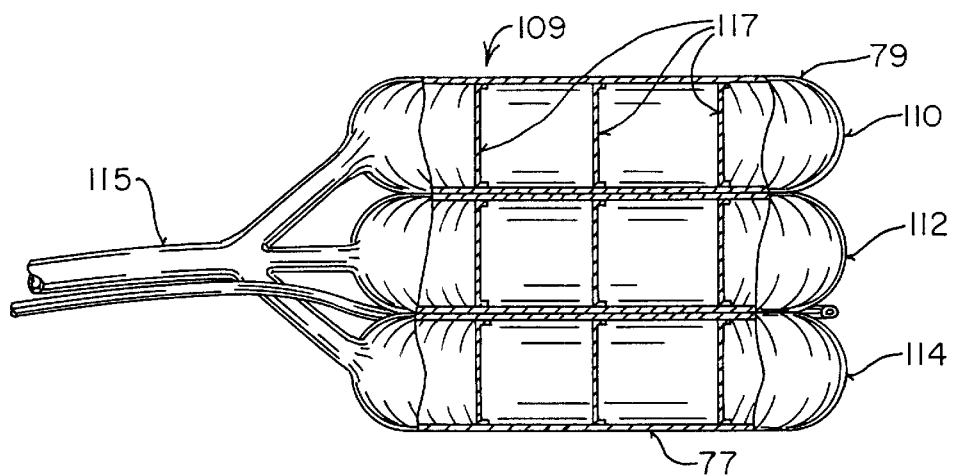
FIG. 3 is a schematic view of another embodiment of the balloon of the present invention showing three stacked balloons and string-like restraints for limiting the expansion of the balloon in directions of inflation.

Still another embodiment of the invention is shown in FIG. 3 which is similar to FIG. 1 except that it is round and not a doughnut and includes an inflatable device 109 having three balloon units 110, 112 and 114 which are inflatable and which have string-like restraints 117 which limit the expansion of the balloon units in a direction transverse to the longitudinal axes of the balloon units. The restraints are made of the same or similar material as that of the balloon so that they have some resilience but substantially no expansion capability.

A tube system 115 is provided to direct liquid under pressure into balloon units 110, 112 and 114 so that liquid can be used to inflate the balloon units when placed inside the bone in a deflated state. Following the proper inflation and compaction of the bone marrow, the balloon can be removed by deflating it and pulling it outwardly of the bone being treated. The restraints keep the opposed sides 77 and 79 substantially flat and parallel with each other.

Figure 10:
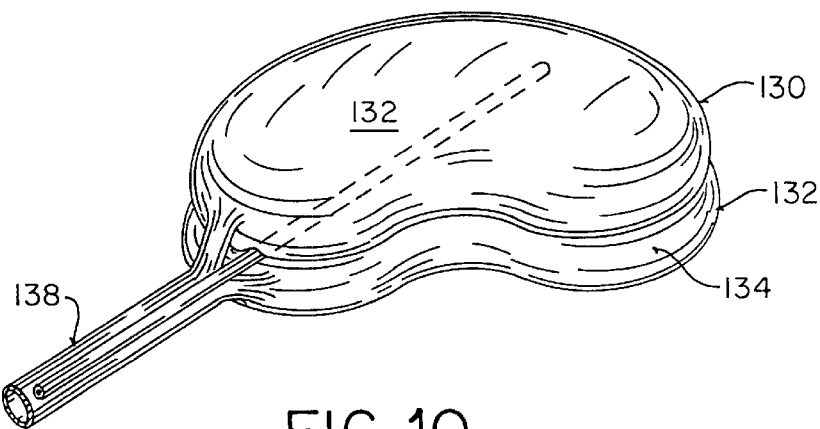
FIG. 10 is a perspective view of another embodiment of the balloon of the present invention formed in the shape of a kidney bean.
Figure 11:
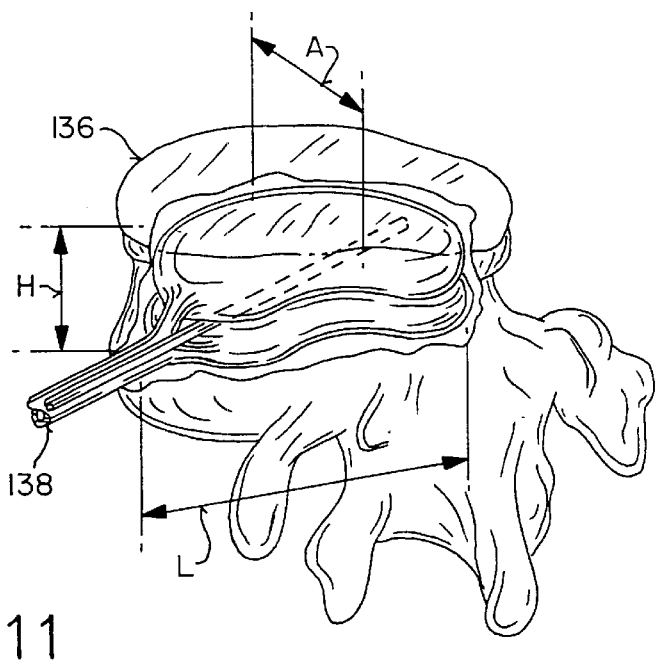
FIG. 11 is a perspective view of the vertebral bone showing the kidney shaped balloon of FIG. 10 inserted in the bone and expanded.

In FIG. 10, another embodiment of the inflatable balloon is shown. The device is a kidney shaped balloon body 130 having a pair of opposed kidney shaped side walls 132 which are adapted to be collapsed and to cooperate with a continuous end wall 134 so that the balloon 130 can be forced into a bone 136 shown in FIG. 11. A tube 138 is used to direct inflating liquid into the balloon to inflate the balloon and cause it to assume the dimensions and location shown vertebral body 136 in FIG. 11. Device 130 will compress the cancellous bone if there is no fracture or collapse of the cancellous bone. The restraints for this action are due to the side and end walls of the balloon.

Figure 12:
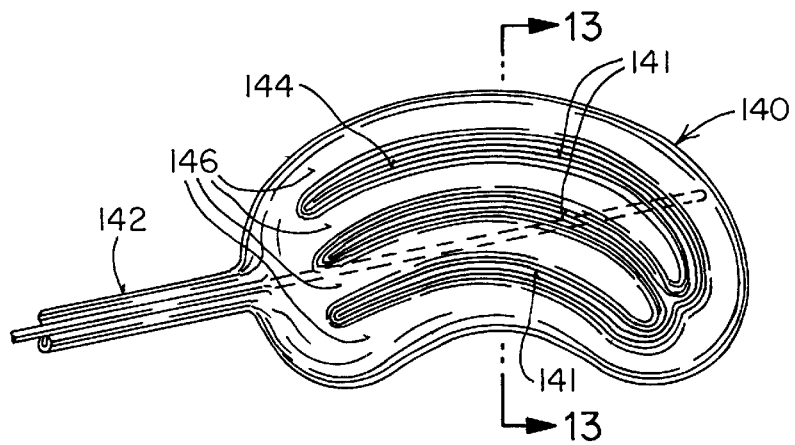
FIG. 12 is a top view of a kidney shaped balloon formed of several compartments by a heating element or branding tool.
Figure 13:
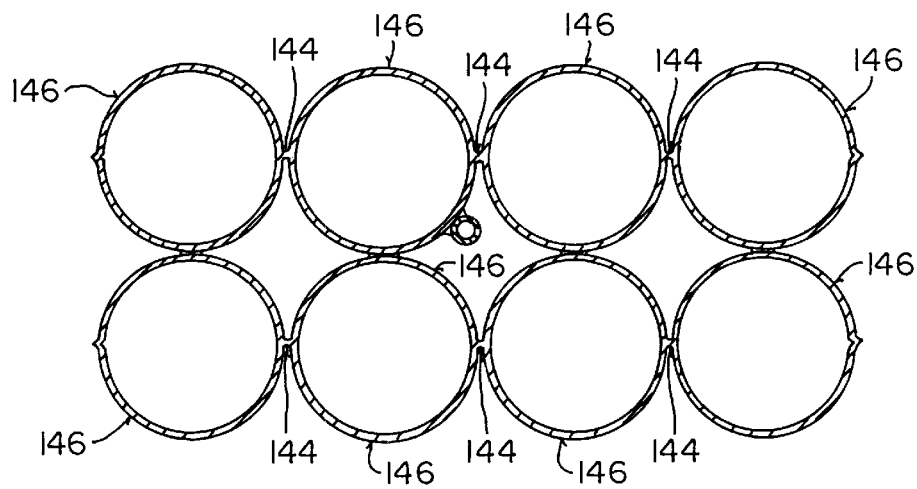
FIG. 13 is a cross-sectional view taken along line 13—13 of FIG. 12 but with two kidney shaped balloons that have been stacked.

FIG. 12 shows a balloon 140 which is also kidney shaped and has a tube 142 for directing an inflatable liquid into the tube for inflating the balloon. The balloon is initially a single chamber bladder but the bladder can be branded along curved lines or strips 141 to form attachment lines 144 which take the shape of side-by-side compartments 146 which are kidney shaped as shown in FIG. 13. The branding causes a welding of the two sides of the bladder to occur since the material is standard medical balloon material, which is similar to plastic and can be formed by heat.

Figure 14:
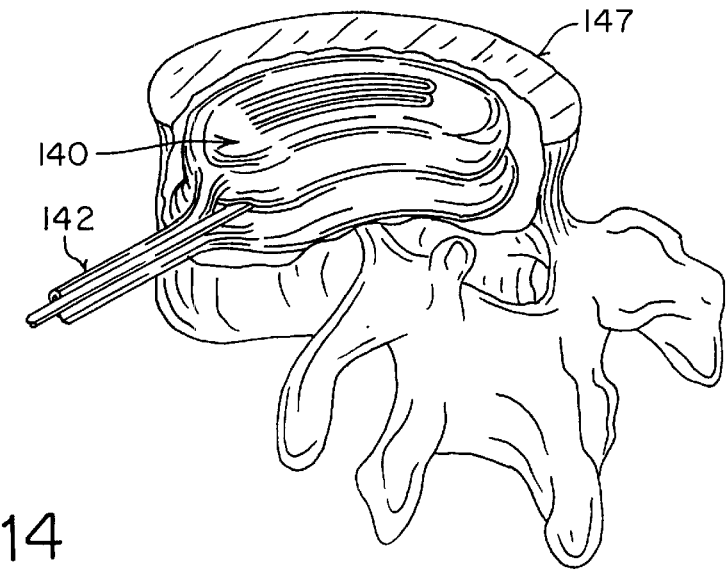
FIG. 14 is a view similar to FIG. 11 but showing the stacked kidney shaped balloon of FIG. 13 in the vertebral bone.

FIG. 14 is a perspective view of a vertebral body 147 containing the balloon of FIG. 12, showing a double stacked balloon 140 when it is inserted in vertebral bone 147.

Figure 15:
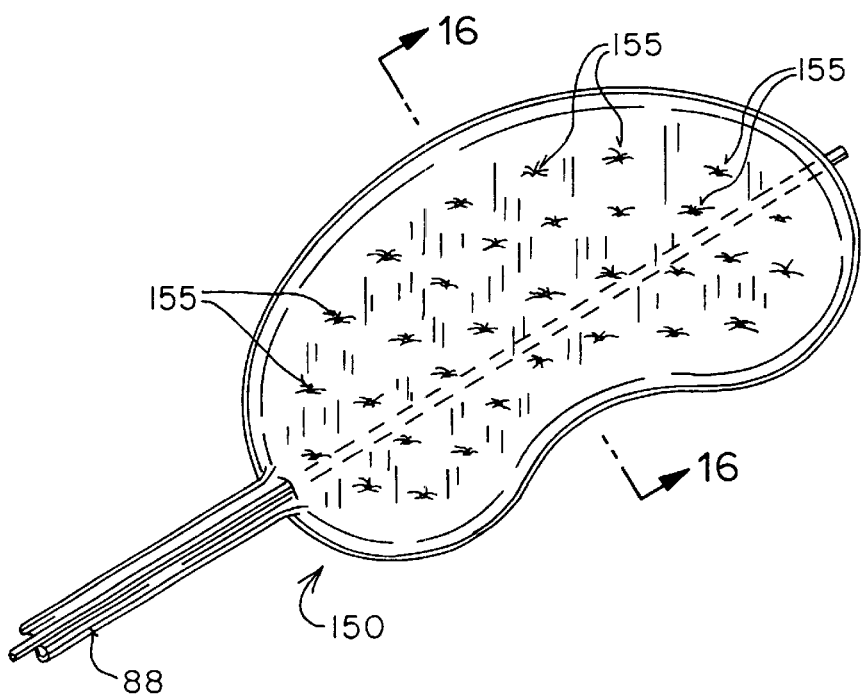
FIG. 15 is a top view of a kidney balloon showing outer tufts holding inner strings in place interconnecting the top and bottom walls of the balloon.
Figure 16:
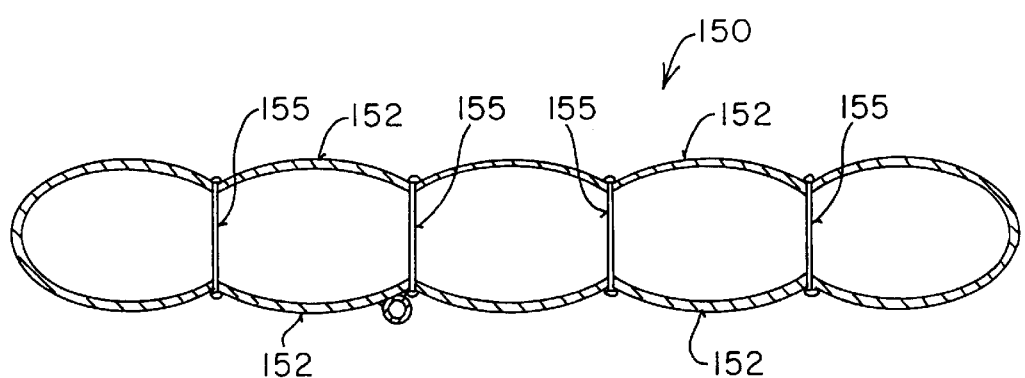
FIG. 16 is a cross sectional view taken along lines 16—16 of FIG. 15.

FIG. 15 is a view similar to FIG. 10 except that tufts 155, which are string-like restraints, extend between and are connected to the side walls 152 of inflatable device 150 and limit the expansion of the side walls with respect to each other, thus rendering the side walls generally parallel with each other. Tube 88 is used to fill the kidney shaped balloon with an inflating liquid in the manner described above.

The dimensions for the vertebral body balloon will vary across a broad range. The heights (H, FIG. 11) of the vertebral body balloon for both lumbar and thoracic vertebral bodies typically range from 0.5 cm to 3.5 cm. The anterior to posterior (A, FIG. 11) vertebral body balloon dimensions for both lumbar and thoracic vertebral bodies range from 0.5 cm to 3.5 cm. The side to side (L, FIG. 11) vertebral body dimensions for thoracic vertebral bodies will range from 0.5 cm to 3.5 cm. The side to side vertebral body dimensions for lumbar vertebral bodies will range from 0.5 cm to 5.0 cm.

The eventual selection of the appropriate balloon for, for instance, a given vertebral body is based upon several factors. The anterior-posterior (A-P) balloon dimension for a given vertebral body is selected from the CT scan or plain film x-ray views of the vertebral body. The A-P dimension is measured from the internal cortical wall of the anterior cortex to the internal cortical wall of the posterior cortex of the vertebral body. In general, the appropriate A-P balloon dimension is 5 to 7 millimeters less than this measurement.

The appropriate side to side balloon dimensions for a given vertebral body is selected from the CT scan or from a plain film x-ray view of the vertebral body to be treated. The side to side distance is measured from the internal cortical walls of the side of the vertebral bone. In general, the appropriate side to side balloon dimension is 5 to 7 millimeters less than this measurement by the addition of the lumbar vertebral body tends to be much wider than side to side dimension then their A-P dimension. In thoracic vertebral bodies, the side to side dimension and their A-P dimensions are almost equal.

The height dimensions of the appropriate vertebral body balloon for a given vertebral body is chosen by the CT scan or x-ray views of the vertebral bodies above and below the vertebral body to be treated. The height of the vertebral bodies above and below the vertebral body to be treated are measured and averaged.

This average is used to determine the appropriate height dimension of the chosen vertebral body balloon.

Balloons for Long Bones

Long bones which can be treated with the use of balloons of the present invention include distal radius (larger arm bone at the wrist), proximal tibial plateau (leg bone just below the knee), proximal humerus (upper end of the arm at the shoulder), and proximal femoral head (leg bone in the hip).

Distal Radius Balloon

For the distal radius, a balloon 160 is shown in the distal radius 152 and the balloon has a shape which approximates a pyramid but more closely can be considered the shape of a humpbacked banana in that it substantially fills the interior of the space of the distal radius to force cancellous bone 154 lightly against the inner surface 156 of cortical bone 158.

Figures 17A, 17B:
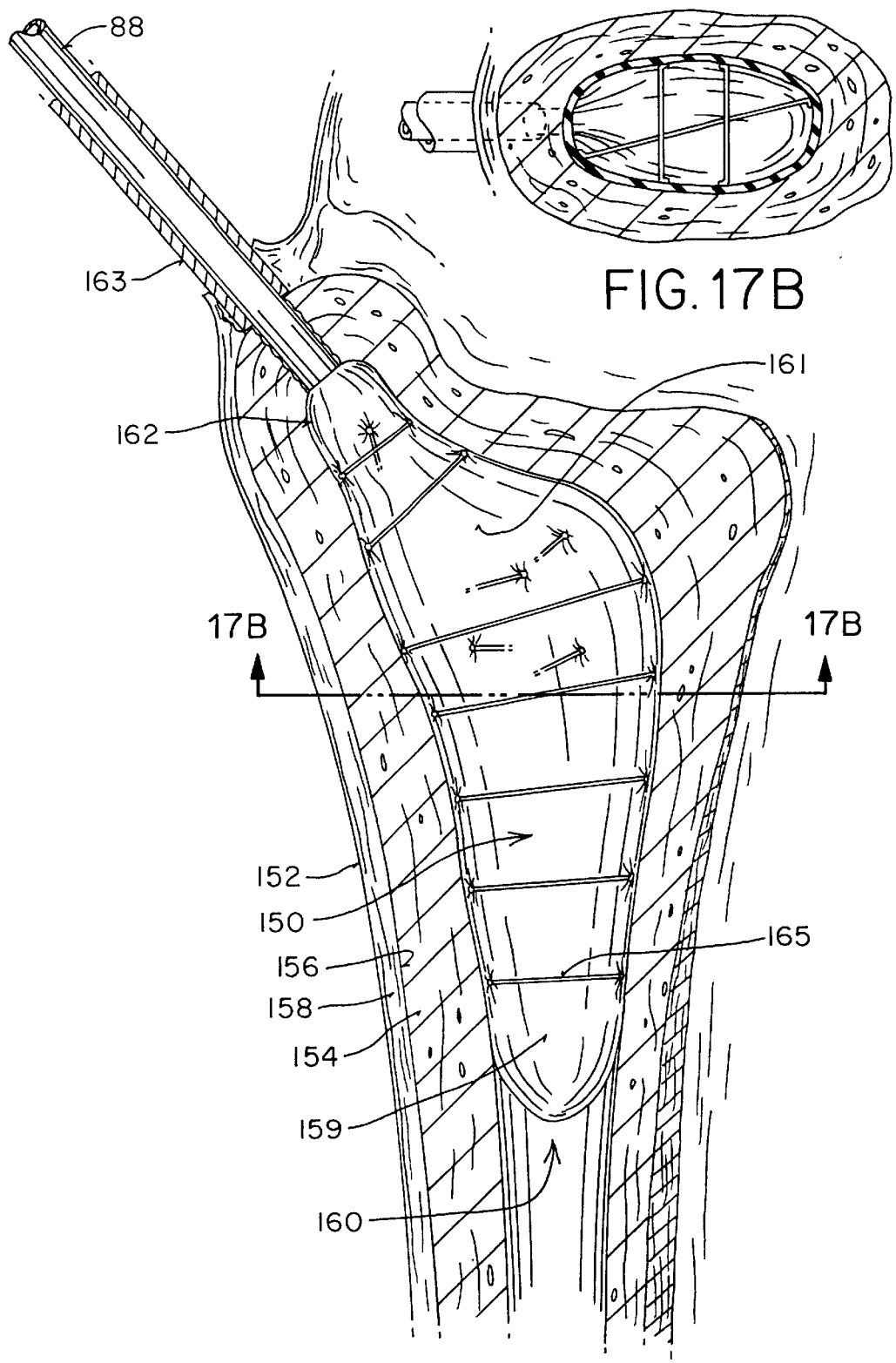
FIG. 17A is a dorsal view of a humpback banana balloon in a right distal radius.
FIGS. 17B is a cross sectional view of FIG. 17A taken along line 17B—17B of FIG. 17A.

The balloon 160 has a lower, conical portion 159 which extends downwardly into the hollow space of the distal radius 152, and this conical portion 159 increases in cross section as a central distal portion 161 is approached. The cross section of the balloon 160 is shown at a central location (FIG. 17B) and this location is near the widest location of the balloon. The upper end of the balloon, denoted by the numeral 162, converges to the catheter 88 for directing a liquid into the balloon for inflating the same to force the cancellous bone against the inner surface of the cortical bone. The shape of the balloon 160 is determined and restrained by tufts formed by string restraints 165. These restraints are optional and provide additional strength to the balloon body 160, but are not required to achieve the desired configuration. The balloon is placed into and taken out of the distal radius in the same manner as that described above with respect to the vertebral bone.

The dimensions of the distal radius balloon vary as follows:

The proximal end of the balloon (i.e. the part nearest the elbow) is cylindrical in shape and will vary from 0.5×0.5 cm to 1.8×1.8 cm.

The length of the distal radius balloon will vary from 1.0 cm to 12.0 cm.

The widest medial to lateral dimension of the distal radius balloon, which occurs at or near the distal radio-ulnar joint, will measure from 1.0 cm to 2.5 cm.

The distal anterior-posterior dimension of the distal radius balloon will vary from 0.5 to 3.0 cm.

Proximal Humerus Fracture Balloon

The selection of the appropriate balloon size to treat a given fracture of the distal radius will depend on the radiological size of the distal radius and the location of the fracture.

Figure 18:
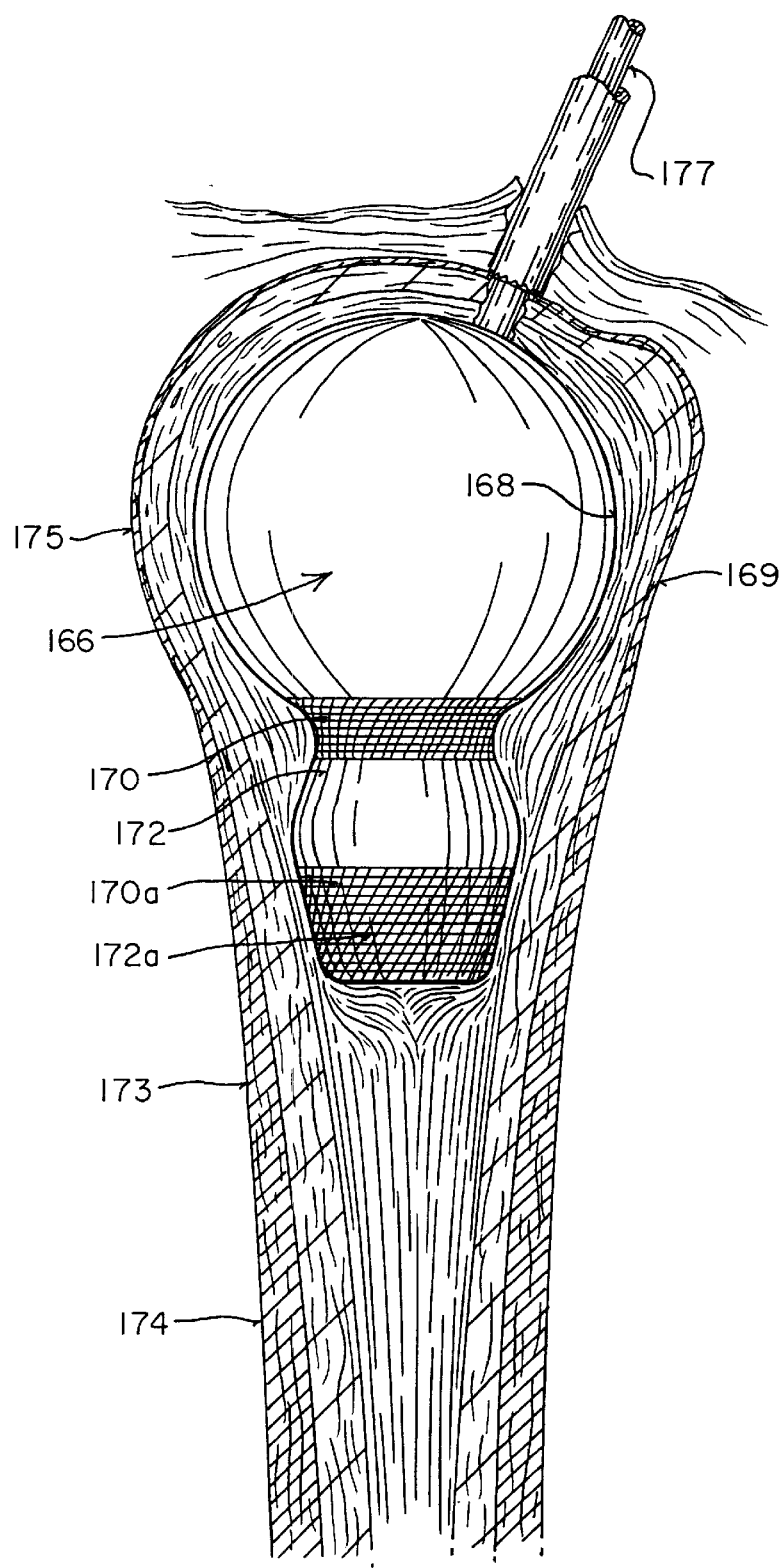
FIG. 18 is a spherical balloon with a base in a proximal humerus viewed from the front (anterior) of the left proximal humerus.

In the case of the proximal humerus 169, a balloon 166 shown in FIG. 18 is spherical and has a base design. It compacts the cancellous bone 168 in a proximal humerus 169. A mesh 170, embedded or laminated and/or winding, may be used to form a neck 172 on the balloon 166, and second mesh 170a may be used to conform the bottom of the base 172a to the shape of the inner cortical wall at the start of the shaft. These restraints provide additional strength to the balloon body, but the configuration can be achieved through molding of the balloon body. This is so that the cancellous bone will be as shown in the compacted region surrounding the balloon 166 as shown in FIG. 18. The cortical bone 173 is relatively wide at the base 174 and is thin-walled at the upper end 175. The balloon 166 has a feed tube 177 into which liquid under pressure is forced into the balloon to inflate it to lightly compact the cancellous bone in the proximal humerus. The balloon is inserted into and taken out of the proximal humerus in the same manner as that described above with respect to the vertebral bone.

The dimensions of the proximal humerus fracture balloon vary as follows:

The spherical end of the balloon will vary from 1.0×1.0 cm to 3.0×3.0 cm.

The neck of the proximal humeral fracture balloon will vary from 0.8×0.8 cm to 3.0×3.0 cm.

The width of the base portion or distal portion of the proximal numeral fracture balloon will vary from 0.5×0.5 cm to 2.5×2.5 cm.

The length of the balloon will vary from 4.0 cm to 14.0 cm.

The selection of the appropriate balloon to treat a given proximal humeral fracture depends on the radiologic size of the proximal humerus and the location of the fracture.

Proximal Tibial Plateau Fracture Balloon

Figure 19A:
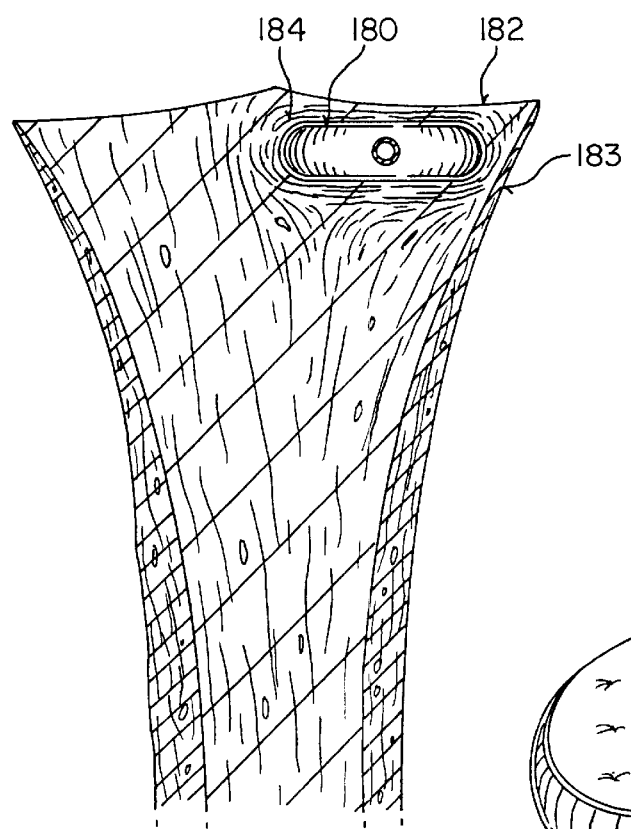
FIG. 19A is the front (anterior) view of the proximal tibia with the elliptical cylinder balloon introduced beneath the medial tibial plateau.
Figure 19B:
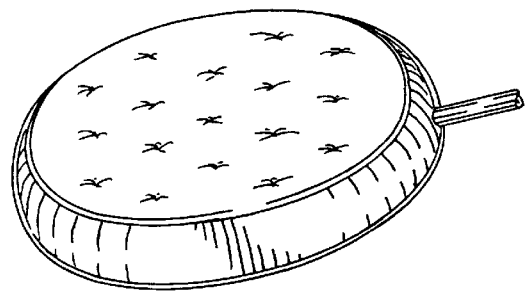
FIG. 19B is a three quarter view of the balloon of FIG. 19A.
Figure 19C:
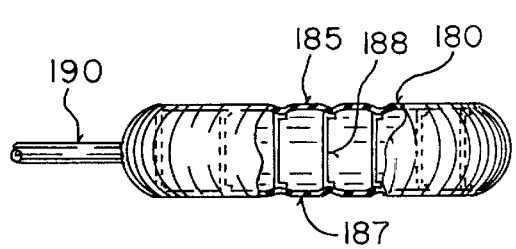
FIG. 19C is a side elevational view of the balloon of FIG. 19A.
Figure 19D:
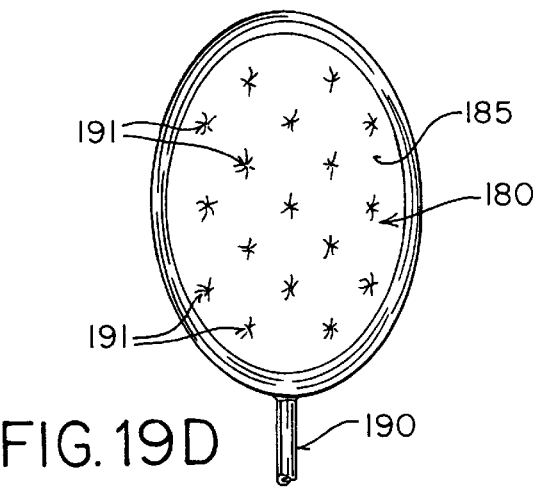
FIG. 19D is a top plan view of the balloon of FIG. 19A.

The tibial fracture is shown in FIG. 19A in which a balloon 180 is placed in one side 182 of a tibia 183. The balloon, when inflated, compacts the cancellous bone in the layer 184 surrounding the balloon 180. A cross section of the balloon is shown in FIG. 19C wherein the balloon has a pair of opposed sides 185 and 187 which are interconnected by restraints 188 which can be in the form of strings or flexible members of any suitable construction. The main purpose of the restraints is to make the sides 185 and 187 substantially parallel with each other and non-spherical. A tube 190 is coupled to the balloon 180 to direct liquid into and out of the balloon. The ends of the restraints are shown in FIGS. 19B and 19D and denoted by the numeral 191. The balloon is inserted into and taken out of the tibia in the same manner as that described above with respect to the vertebral bone. FIG. 19B shows a substantially circular configuration for the balloon; whereas, FIG. 19D shows a substantially elliptical version of the balloon.

The dimensions of the proximal tibial plateau fracture balloon vary as follows:

The thickness or height of the balloon will vary from 0.5 cm to 5.0 cm.

The anterior/posterior (front to back) dimension will vary from 1.0 cm to 6.0 cm.

The side to side (medial to lateral) dimension will vary from 1.0 cm to 6.0 cm.

The selection of the appropriate balloon to treat a given tibial plateau fracture will depend on the radiological size of the proximal tibial and the location of the fracture.

Femoral Head Balloon

Figures 20, 20A:
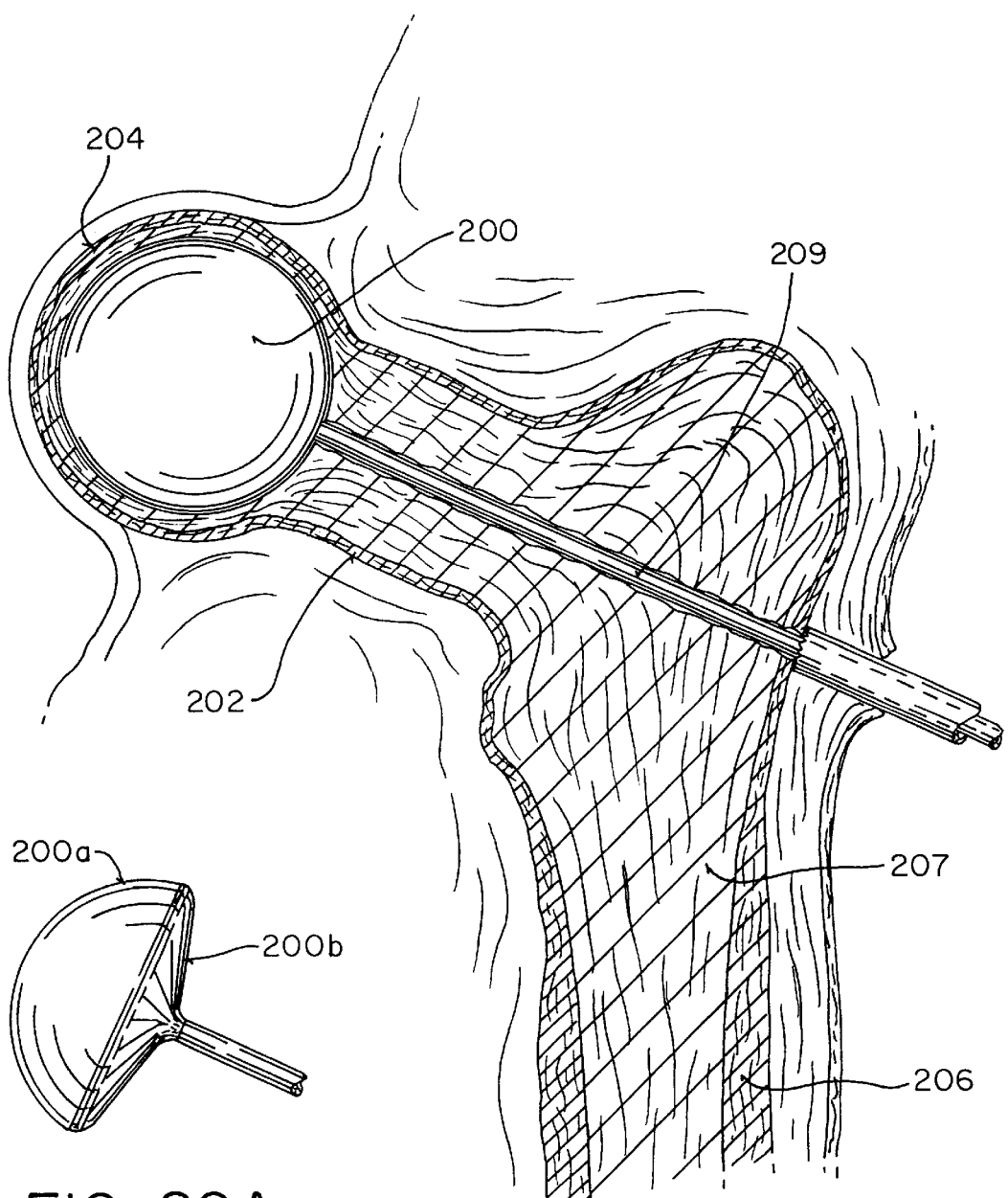
FIG. 20 is a spherically shaped balloon for treating avascular necrosis of the head of the femur (or humerus) as seen from the front (anterior) of the left hip.
FIG. 20A is a side view of a hemispherically shaped balloon for treating avascular necrosis of the head of the femur (or humerus).

In the case of the femoral head, a balloon 200 is shown as having been inserted inside the cortical bone 202 of the femoral head which is thin at the outer end 204 of the femur and which can increase in thickness at the lower end 206 of the femur. The cortical bone surrounds the cancellous bone 207 and this bone is compacted by the inflation of balloon 200. The tube for directing liquid for inflation purposes into the balloon is denoted by the numeral 209. It extends along the femoral neck and is directed into the femoral head which is generally spherical in configuration. FIG. 20A shows that the balloon, denoted by the numeral 200a, can be hemispherical as well as spherical, as shown in FIG. 20. The balloon 200 is inserted into and taken out of the femoral head in the same manner as that described with respect to the vertebral bone. The hemispherical shape is maintained in this example by bonding overlapping portions of the bottom, creating pleats 200b as shown in FIG. 20A.

The dimensions of the femoral head balloon vary as follows:

The diameter of the femoral head balloon will vary from 1.0 cm to up to 4.5 cm. The appropriate size of the femoral head balloon to be chosen depends on the radiological or CT scan size of the head of the femur and the location and size of the avascular necrotic bone. The dimensions of the hemispherical balloon are the same as the those of the spherical balloon, except that approximately one half is provided.

What is claimed is:

1. A device for insertion into a vertebral body to apply a force capable of compacting cancellous bone and moving fractured cortical bone, the device including a catheter extending along an axis and having a distal end sized and configured for insertion through a cannula into the vertebral body, the catheter carrying near its distal end an inflatable body having a wall sized and configured for passage within the cannula into the vertebral body when the inflatable body is in a collapsed condition, the wall being further sized and configured to apply the force in response to expansion of the inflatable body within the vertebral body, the wall including opposed side surfaces extending along an elongated longitudinal axis that is substantially aligned with the axis of the catheter, the wall including changes in wall thickness which restrain the opposed side surfaces from expanding beyond a substantially flat condition along the elongated longitudinal axis.

2. A device for insertion into a vertebral body to apply a force capable of compacting cancellous bone and moving fractured cortical bone, the device including a catheter extending along an axis and having a distal end sized and configured for insertion through a cannula into the vertebral body, the catheter carrying near its distal end an inflatable body having a wall sized and configured for passage within the cannula into the vertebral body when the inflatable body is in a collapsed condition, the wall being further sized and configured to apply the force in response to expansion of the inflatable body within the vertebral body, the wall including opposed side surfaces extending along an elongated longitudinal axis that is substantially aligned with the axis of the catheter, the wall including an internal restraint which restrains the opposed side surfaces from expanding beyond a substantially flat condition along the elongated longitudinal axis.

3. A device according to claim 2 wherein the internal restraint includes mesh material.

4. A device according to claim 2 wherein the internal restraint includes string material.

5. A device according to claim 2 wherein the internal restraint includes woven material.

6. A device according to claim 2 wherein the internal restraint includes a seam.

7. A device according to claim 2 wherein the internal restraint includes an essentially non-elastic material.

8. A device for insertion into a vertebral body to apply a force capable of compacting cancellous bone and moving fractured cortical bone, the device including a catheter extending along an axis and having a distal end sized and configured for insertion through a cannula into the vertebral body, the catheter carrying near its distal end an inflatable body having a wall sized and configured for passage within the cannula into the vertebral body when the inflatable body is in a collapsed condition, the wall being further sized and configured to apply the force in response to expansion of the inflatable body within the vertebral body, the wall including opposed side surfaces extending along an elongated longitudinal axis that is substantially aligned with the axis of the catheter, the wall including an external restraint which restrains the opposed side surfaces from expanding beyond a substantially flat condition along the elongated longitudinal axis.

9. A device according to claim 8 wherein the external restraint includes mesh material.

10. A device according to claim 8 wherein the external restraint includes string material.

11. A device according to claim 8 wherein the external restraint includes woven material.

12. A device according to claim 8 wherein the external restraint includes a seam.

13. A device according to claim 8 wherein the external restraint includes an essentially non-elastic material.

14. A device according to claim 1 or 2 or 8 wherein the inflatable body comprises a balloon.

* * * * *

UNITED STATES PATENT AND TRADEMARK OFFICE
CERTIFICATE OF CORRECTION

PATENT NO. : 6,423,083 B2
DATED : July 23, 2002
INVENTOR(S) : Mark A. Reiley, Arie Scholten and Karen Talmadge It is certified that error appears in the above-identified patent and that said Letters Patent is hereby corrected as shown below:

Title page,
Item [60], Related U.S. Application Data, after "08/788,786, file on Jan. 23, 1997" delete the period "." and insert -- ; which is a continuation of application Serial No. 08/188,244 filed on January 26, 1994 (now abandoned). --

Signed and Sealed this

Twenty-second Day of March, 2005

JON W. DUDAS
*Director of the United States Patent and Trademark Office*